United States Patent
Kammer et al.

(10) Patent No.: US 9,326,667 B2
(45) Date of Patent: May 3, 2016

(54) ANTI-FOGGING AND CLEANING APPARATUS FOR MEDICAL SCOPES

(75) Inventors: Patrick Kammer, Greensboro, NC (US); Mark Martel, Belews Creek, NC (US); Todd Cassidy, Mocksville, NC (US)

(73) Assignee: C CHANGE SURGICAL LLC, Winston-Salem, NC (US)

( * ) Notice: Subject to any disclaimer, the term of this patent is extended or adjusted under 35 U.S.C. 154(b) by 2322 days.

(21) Appl. No.: 12/258,192

(22) Filed: Oct. 24, 2008

(65) Prior Publication Data

US 2009/0112057 A1    Apr. 30, 2009

Related U.S. Application Data

(60) Provisional application No. 61/000,482, filed on Oct. 26, 2007.

(51) Int. Cl.
*A61B 1/00* (2006.01)
*A61B 1/12* (2006.01)
*A61B 1/06* (2006.01)

(52) U.S. Cl.
CPC ..................................... *A61B 1/127* (2013.01)

(58) Field of Classification Search
USPC ......... 600/102, 114, 133, 121, 153–159, 169; 248/148, 152; 219/441; 134/95.3
See application file for complete search history.

(56) References Cited

U.S. PATENT DOCUMENTS

| | | | |
|---|---|---|---|
| 1,791,254 A | | 2/1931 | Von Brockdorff |
| 3,299,883 A | * | 1/1967 | Rubens ......................... 600/102 |
| 4,064,886 A | * | 12/1977 | Heckele ....................... 134/95.3 |
| 4,288,882 A | * | 9/1981 | Takeuchi ........................... 15/88 |
| 5,207,213 A | | 5/1993 | Auhll et al. ....................... 128/6 |
| 5,309,895 A | | 5/1994 | Yabe ................................ 128/6 |
| 5,392,766 A | | 2/1995 | Masterson et al. ............... 128/4 |
| 5,464,008 A | | 11/1995 | Kim .............................. 600/157 |
| 5,487,376 A | * | 1/1996 | Yabe et al. .................... 600/121 |
| 5,511,568 A | * | 4/1996 | Bowman et al. ........... 134/102.2 |
| 5,518,146 A | | 5/1996 | Mattei .............................. 222/1 |
| 5,549,543 A | | 8/1996 | Kim .............................. 600/169 |

(Continued)

FOREIGN PATENT DOCUMENTS

WO    WO 2005/096916 A1    10/2005

OTHER PUBLICATIONS

"Applied Scope Warmer", Applied Medical, 4 pgs (2006). Third page is an enlarged view of the lower left portion of p. 2. Fourth page is an enlarged view of the lower right portion of p. 2.

(Continued)

*Primary Examiner* — Anhtuan T Nguyen
*Assistant Examiner* — Timothy J Neal
(74) *Attorney, Agent, or Firm* — Fredrikson & Byron, P.A.

(57) ABSTRACT

An apparatus and method for warming a medical scope to a temperature at or near body temperature in order to prevent fogging and remove debris. A system for warming medical scopes and a variety of other medical items is to be used in conjunction with a liquid warming device for heating sterile fluids. The anti-fogging apparatus is described with emphasis on the properties of said apparatus and its interaction with a liquid warming device with a removable basin. Also disclosed are various desirable aspects for an apparatus used to warm and clean medical scopes and other medical items before, during and after medical procedures.

16 Claims, 22 Drawing Sheets

(56) References Cited

U.S. PATENT DOCUMENTS

| | | | | |
|---|---|---|---|---|
| 5,569,163 | A | 10/1996 | Francis et al. | 600/133 |
| 5,647,840 | A | 7/1997 | D'Amelio et al. | 600/169 |
| 5,651,757 | A | 7/1997 | Meckstroth | 600/169 |
| 5,785,644 | A | 7/1998 | Grabover et al. | 600/131 |
| 5,863,287 | A * | 1/1999 | Segawa | 600/121 |
| 5,910,106 | A | 6/1999 | Morgan et al. | 600/169 |
| 6,167,296 | A | 12/2000 | Shahidi | 600/427 |
| 6,234,635 | B1 | 5/2001 | Seitzinger et al. | 359/512 |
| 6,354,992 | B1 | 3/2002 | Kato | 600/157 |
| 6,547,724 | B1 * | 4/2003 | Soble et al. | 600/156 |
| 6,591,130 | B2 | 7/2003 | Shahidi | 600/424 |
| 6,712,479 | B1 | 3/2004 | Seitzinger et al. | 359/512 |
| 7,128,275 | B2 * | 10/2006 | Kammer et al. | 236/1 C |
| 7,311,660 | B2 | 12/2007 | Gomez | 600/169 |
| 7,560,667 | B2 * | 7/2009 | Kammer et al. | 219/432 |
| 2005/0234301 | A1 | 10/2005 | Gomez | 600/169 |

OTHER PUBLICATIONS

International Search Report and Written Opinion From Corresponding PCT Application No. PCT/US2008/081326, May 27, 2009 (12 pgs).

\* cited by examiner

ANTI-FOGGING AND CLEANING APPARATUS FOR MEDICAL SCOPES

This application claims priority to and incorporates by reference U.S. Provisional Patent Application No. 61/000, 482. Basins suitable for use with the present disclosure are shown in U.S. Design Patents U.S. Pat. No. D546,943S, U.S. Pat. No. D546,944 S, U.S. Pat. No. D547,444 for hospital basins. While the teachings of the present disclosure may be used with a variety of liquid warming devices, one suitable device is described in commonly assigned U.S. Pat. No. 7,128,275 for Liquid Warming Device With Basin. The '275 patent is incorporated herein by reference in its entirety. Another application with common assignee is co-pending with the present application. The application is for a Heating Element for Liquid Warming Device with U.S. Ser. No. 11/209,430. The inventive aspects of heating elements disclosed in that application can be advantageously used with the present disclosure. The co-pending application is incorporated herein by reference in its entirety.

BACKGROUND

1. Field of the Disclosure

This disclosure relates to improvements in methods and apparatus for warming and cleaning of medical scopes (laparoscopes, endoscopes, arthroscopes, and other medical scopes) and of a variety of medical items used in medical procedures. More specifically, this disclosure relates to an apparatus for the warming and cleaning of medical scopes and other medical items used in conjunction with a liquid warming device with a removable basin.

2. Background of the Problem Addressed

Devices for heating various scopes inserted into the body for a variety of medical uses and procedures are known in the art. Visual clarity is a cornerstone of safe surgery; however, lens fogging occurs when cool scopes are inserted into warm, moist intracorporeal cavities. This fogging obscures safe visualization and delays procedures until visual clarity is established. Establishing visual clarity typically requires several costly minutes as a medical scope equilibrates from the typical temperature in a surgical suite of 68 degrees Fahrenheit with the warm, moist environment within the body. It is acknowledged that lens fogging reduces patient safety and increases procedure time and cost. Improvements to the surgical process that decrease the amount of time for the surgery and thus decrease the amount of time that a patient is under anesthesia (either local or general anesthesia). Decreasing the amount of time that a patient is subject to anesthesia while achieving the same surgical goal is considered advantageous.

The prior art includes various warming devices to warm the distal and/or proximal lens of medical scopes. In this context, proximal is relative to the user of the scope with distal being away from the end user and possibly within the patient. For a medical scope, proximal would be the eyepiece and distal would be the working end of the scope that is placed within a patient. Scope lens fogging remains a nagging problem occurring in almost all procedures.

As noted in U.S. Pat. No. 6,712,479, antifogging liquids that are wiped on the lens are common, but are criticized for possibly scratching the optic and for only briefly addressing the problem. Heating the medical scope to more closely match the temperature of the body was common but largely abandoned when debris became baked onto the laparoscope. A variation of this latter method is achieved by rinsing the laparoscope after a cold sterilization process with warm sterile water and taking the warmed laparoscope quickly to the surgical field.

For treating a fogged laparoscope in the field, a commercially available product known as the Applied Scope Warmer manufactured by Applied Medical Resources, is a double-walled thermos filled with warm water having padding inside to cushion the lens. A disposable seal is placed over the top of the device to provide insulation while permitting insertion of a single laparoscope. It is reported that the warm water heats one laparoscope sufficiently to clear fogging and has the additional feature of rinsing off debris. This prior art attempt to address the problem provides only limited relief as the Applied Medical Resources device maintains warm fluid for a limited time and warms only one laparoscope.

It is typical in many procedures for up to several different medical scopes to be used and it is not uncommon to use many different medical scopes. Thus frequently more than one and possibly several different medical scopes need to be kept warm and free of debris during any particular part of the surgical procedure.

Various objects, advantages and novel features of the disclosure will be set forth in part either explicitly or implicitly in the description that follows, and in part will become apparent to those skilled in the art upon examination of the following or may be learned by practice of one or more teachings of the present disclosure. The objects and advantages may be realized and attained by means of the instrumentalities and combinations particularly pointed out in the claims that ultimately issue based on this disclosure.

BRIEF DESCRIPTION OF THE FIGURES

The disclosure can be better understood with reference to the set of figures. The components in the figures are not necessarily to scale, emphasis instead being placed upon illustrating the principles of the disclosure. Moreover, in the figures, like reference numerals designate corresponding parts throughout the different views.

DETAILED DESCRIPTION

The present disclosure fits within the larger field of devices for heating sterile surgical fluids. Devices for the heating of sterile surgical liquids are known in the art. In a wide variety of surgical procedures, sterile fluids are used to irrigate the site of the surgery. It is important that the temperature of the fluids used be strictly controlled. As the portion of the brain that regulates body temperature is shut down with general anesthesia, it is important that the introduction of sterile fluids does not cool the body core temperature. Clinical studies have indicated that a range of adverse consequences arise from a change in body core temperature as little as one to three degrees Celsius. The adverse consequences from mild perioperative hypothermia include hypertension and increased vascular resistance, cardiac events, coagulopathy, an increase risk of surgical wound infections, and delays in the body's ability to remove drugs from its systems. An additional potential adverse consequence is shivering which can increase metabolic rate up to 500% and thus increase demands for oxygen and the need to clear carbon dioxide. This list of complications is by no means exhaustive, but it highlights the critical importance in controlling the body core temperature. Careful control of the temperature of sterile irrigation fluids is an important part of controlling body core temperature.

The prior art includes various liquid warming devices to warm sterile fluid. Some are incorporated into a rolling cabinet for placement in a convenient place within the sterile field in an operating room so that sterile fluid is available at an appropriate temperature for uses in the surgery such as irrigation or lavage. It is recognized as desirable that the process for heating the fluid be capable of quickly heating the fluid to bring the fluid to the appropriate temperature. It is also recognized that having the heater apply so much heat that it damages the container used to hold the fluid is undesirable. Use of a heater that can expose personnel to heated surfaces that are hot enough to cause injury is undesirable and in some cases contrary to governmental regulations.

Figure 1:
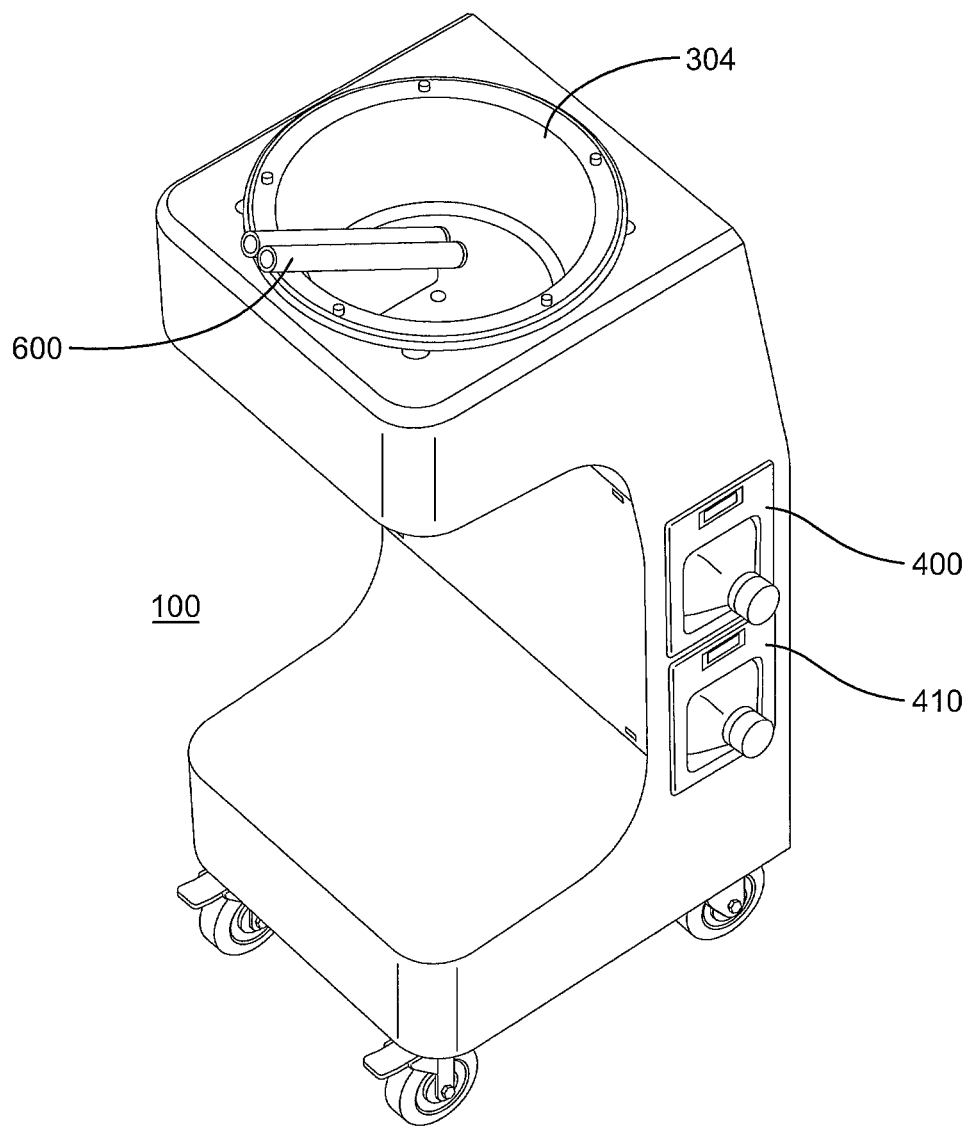
FIG. 1 is a system of components to warm a submerged portion of a medical scope including a scope holder and a liquid warming device.

FIG. 1 shows a fluid warming device 100 with a basin 304 placed into a cavity in the top surface of the fluid warming device 100. In many instances a sterile drape would be placed over the fluid warming device 100 to work in conjunction with the basin 304 to maintain a sterile field to separate the inner and lower portions of the fluid warming device from the sterile field. In order to help provide context, FIG. 1 shows a scope holder analogous to what is shown as scope holder 600 in FIG. 17 below. The scope holder 600 shown in FIG. 1 has two scope tubes to receive one medical scope at a time per scope tube. The heat applied to the sterile liquid placed in the open basin 304 is transferred to portions of the scope holder 600 to heat sterile fluid in the scope holder tubes (and most likely isolated from the sterile fluid in the basin so that the level in the scope holder tube can be held above the level of sterile fluid in the basin). Medical scopes may be inserted into the scope tubes to heat the medical scope to avoid fogging while avoiding baking debris onto the medical scope. The scope holder may be sized and angled so that the handle of the medical scope is conveniently located slightly above and outside of the rim of the basin 304.

Figure 2:
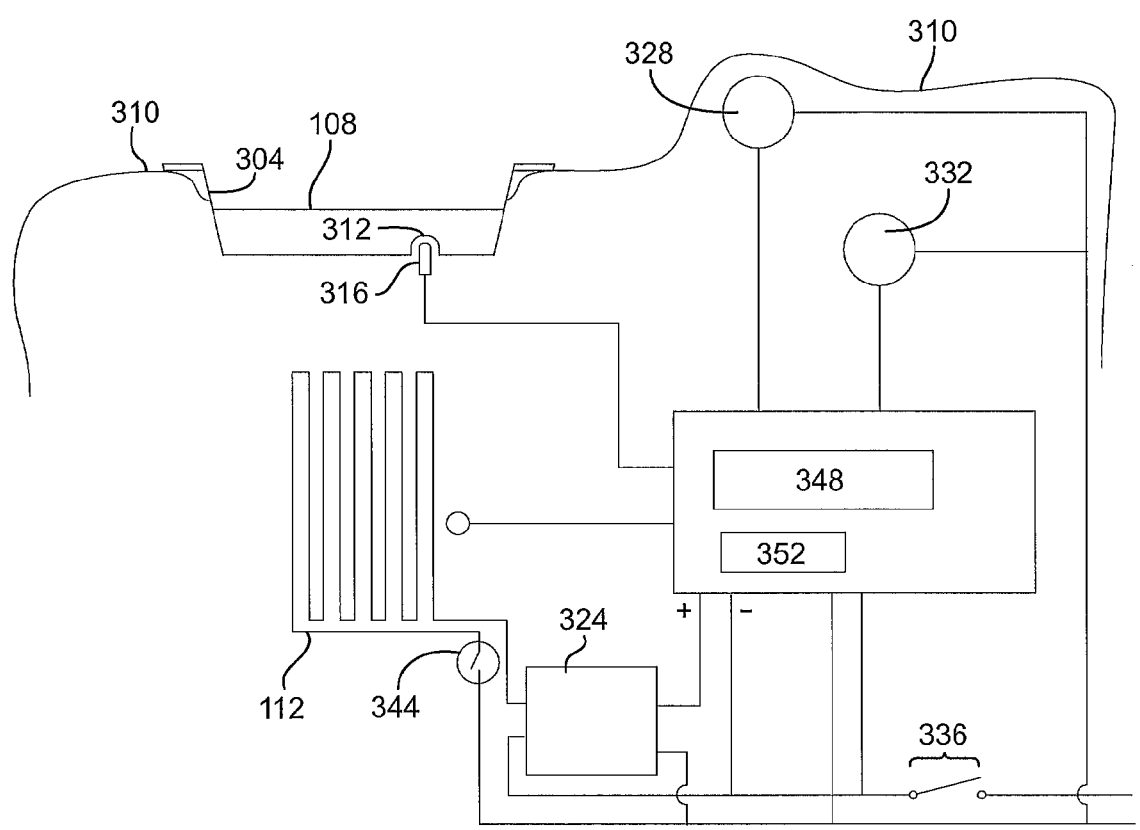
FIG. 2 introduces components of a liquid warming device.

FIG. 2 covers many of the features discussed in now issued U.S. Pat. No. 7,128,275 for Liquid Warming Device With Basin. It may be useful to introduce concepts of a liquid warming device through a discussion of FIG. 2.

The sterile fluid 108 is inside modified basin 304 with integral thermocouple well 312 and temperature sensor 316. The heater 112 selectively applies heat that is transferred to the basin 304 and the fluid 108. The fluid warming device has a main on/off switch 336. Some heating elements come with a mechanical thermostat 344 such as a bimetallic thermostat to provide a secondary protection against a failed control system. This second mechanical thermostat 344 acts as a switch to shut off the heater if the temperature exceeds a set temperature. This should be set to a temperature that is low enough that the mechanical thermostat opens before the heater can overheat an empty basin. For example a mechanical thermostat set for 220 degrees Fahrenheit might be acceptable for use with a basin capable of withstanding permanent exposure to a 300 degree Fahrenheit heat source.

A modified surgical drape 310 may be connected to some combination of the upper rim of the basin 304 or its outside wall so that the basin 304 extends down through the hole in the surgical drape. As the modified surgical drape 310 does not run along the bottom of the basin, the drape 310 does not interfere with the interaction of the thermocouple well 312 and the control system. Nor does the drape 310 get between the bottom of the basin 304 and the heat coming from heater 112 to the bottom of the basin. The drape basin combination would typically be combined together as part of preparing a surgical kit and the drape would encircle the basin bottom with the remainder of the drape folded or pooled in the cavity of the basin so that the basin could be placed into the fluid warming device and once properly positioned, the drape could be unfolded from the basin to cover the top and upper sides of the fluid warming device to maintain a sterile field.

The interaction between the drape 310 and the basin 304 could be a simple interference fit such that the basin once inserted into a hole in the drape stretches the drape so that the drape stays attached to the basin sufficiently for it to maintain the sterile field. Alternatively, the drape could be bonded to the outer wall of the basin or to the underside of the rim of the basin.

FIG. 2 shows drape 310 extending downward to cover the components in FIG. 2. This is illustrative of the point that the drape is used to maintain the sterile field, but one of skill in the art will recognize that individual components shown in FIG. 2 are apt to be inside a housing and not in direct contact with the drape. One exception is the tops of the indicator lamps 328 and 332 conveying status such as the relationship between the current measured temperature and the target temperature (and possibly other items) which must remain visible through the drape. Some controls may be placed outside of the sterile field and thus located below where the drape ends on the liquid warming device.

The target temperature 352 set point for the fluid in the basin 304 may be set by controls at the time of assembly at the manufacturer (not shown here). The target temperature 352 and the current temperature of the fluid can be displayed on a display 348. The display 348 may be placed low on the housing so that these components are below the drape 310 and outside the sterile field. One of skill in the art will recognize that special window could be placed in the drape or the drape could be made of material with optical properties that allow a standard LED display to be read through the drape.

Some implementations of the components shown in FIG. 2 may use a thermocouple well 312 made of a material that conducts heat, such as metal, but is preferably made so as to have low thermal mass in order to be very responsive to changes in the temperature of the sterile fluid. Using a small diameter well and thin gauge material is useful for obtaining a low thermal mass. The thermocouple well can be a hemispheric protrusion into the sterile fluid but could also be some other shape. Preferably the thermocouple well will present a three-dimensional surface of conductive material to the sterile fluid rather than a plate of conductive material at the top of a non-conductive protrusion.

Some basins may be designed so that the thermocouple well is made of the same material as the rest of the basin as this will serve to decrease the cost of fabrication and eliminate the potential for leakage at the border between two dissimilar materials. A thermocouple well incorporated into a polypropylene basin will afford significant responsiveness of the thermocouple in the well as the thermocouple/well combination will be extended out into the fluid.

While FIG. 2 shows a basin/drape combination where the drape does not go between the basin bottom and the liquid warming device, other implementations may use a surgical drape between the basin and the cavity that receives the basin given appropriate adaptations from the component set shown in FIG. 2. Alternatively, a scope warming device could be used in a liquid warming device that uses a drape in a permanent basin shaped cavity.

U.S. Pat. No. 7,128,275 for Liquid Warming Device With Basin describes a number of innovations for the liquid warming device and in particular for the interaction between the liquid warming device and the basin. Some of those details will be revisited in the present disclosure but there is not a need to revisit all the innovative aspects of the '275 patent. Unless specifically stated to the contrary, it is understood that the present disclosure may be used with different liquid warming devices including those that differ from the liquid warming devices described herein to provide context to the present disclosure.

One Scope Warming Solution.

An anti-fogging and cleaning apparatus that works uniquely with a liquid warming device with a basin is disclosed. In the context of this disclosure, a short name for an anti-fogging and cleaning apparatus is a scope holder. (While as a practical matter, there are advantages in general to using a removable basin in a liquid warming device, teachings of the present disclosure may be used with permanent basins including permanent basins that are draped.)

In one implementation, the scope holder can securely hold and warm more than one medical scope of various dimensions in warm fluid for the length of time sufficient to prepare for and complete a medical procedure. In one implementation, the scope holder is made with a base that makes direct thermal contact with the floor of the removable basin and is made of material with high thermal conductivity. Typically, this would be a metal but it could be any material that has a higher level of thermal conductivity than the sterile liquid.

In one implementation, the scope holder base transfers thermal energy to a sleeve ("scope tube") made of a material with lower thermal conductivity than the scope holder base.

In another implementation the base and the sleeve are made of the same material with the same thermal conductivity as this choice lowers the cost of fabrication of the scope holders.

In some implementations, the scope holder has openings at both ends to facilitate cleaning. The openings at the lower end may be reversibly sealed using seals, caps, plugs or some suitable leak prevention system made of non-abrasive material. In some implementations, the scope holder can securely hold scopes of various dimensions by using fittings made of a non-abrasive material that securely grip or cradle the scopes nearer to the proximal than distal end.

FIGS. 3-24 show a set of views of one implementation of a scope holder made in accordance with some teachings of the present disclosure.

Figure 3:
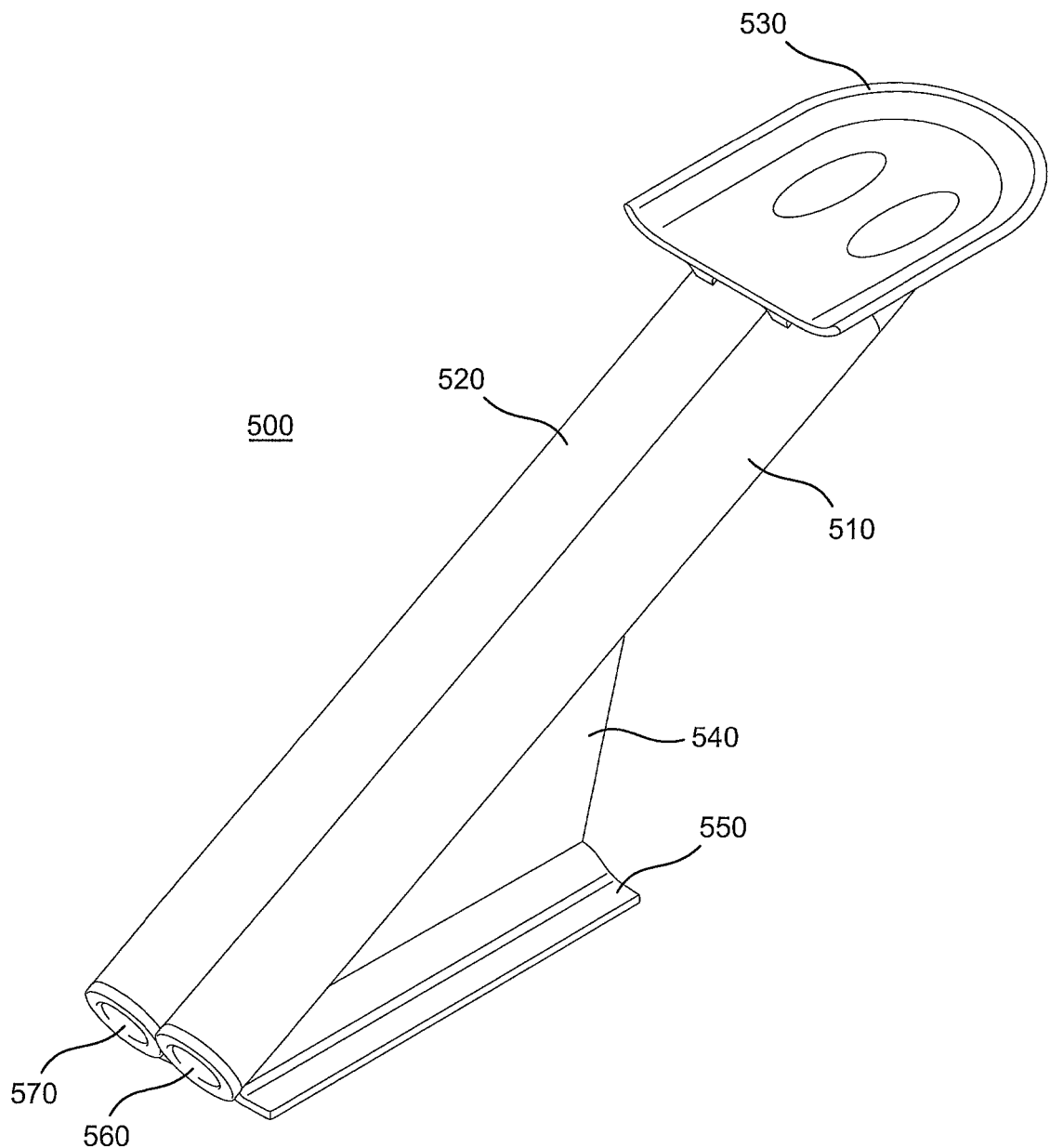
FIG. 3 shows a perspective view of one scope holder 500.
Figure 4:
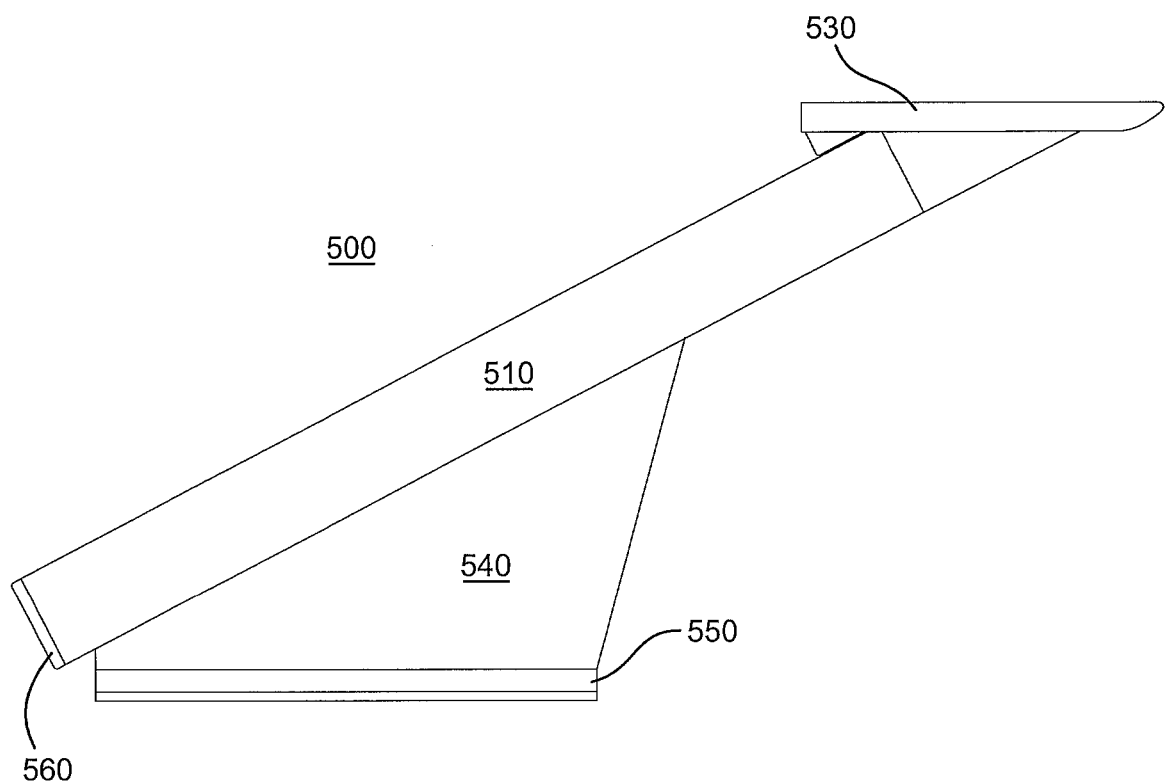
FIGS. 4 and 5 provide side views of scope holder 500.
Figure 5:
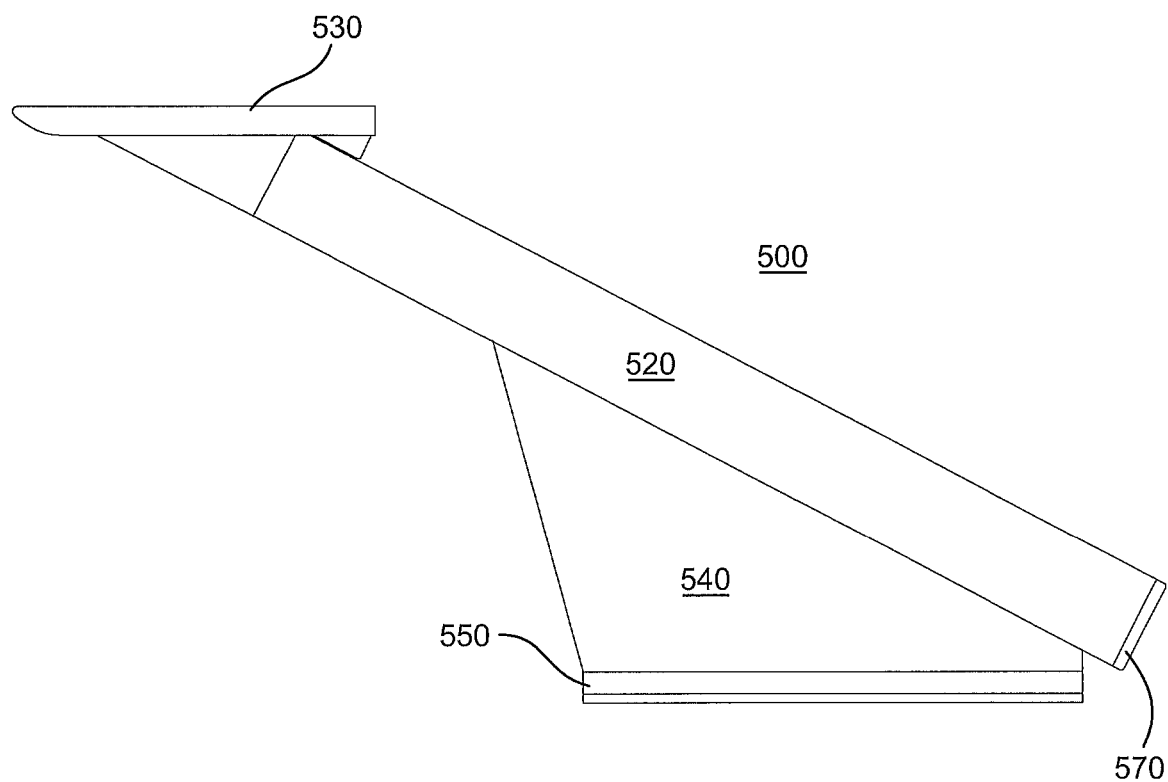

FIG. 3 shows a perspective view of one scope holder 500. The components in this scope holder are two scope tubes 510 and 520, a top plug 530, scope stand 540, stand base 550 and tube plugs 560 and 570. FIGS. 4 and 5 provide side views of the same components.

Figure 6:
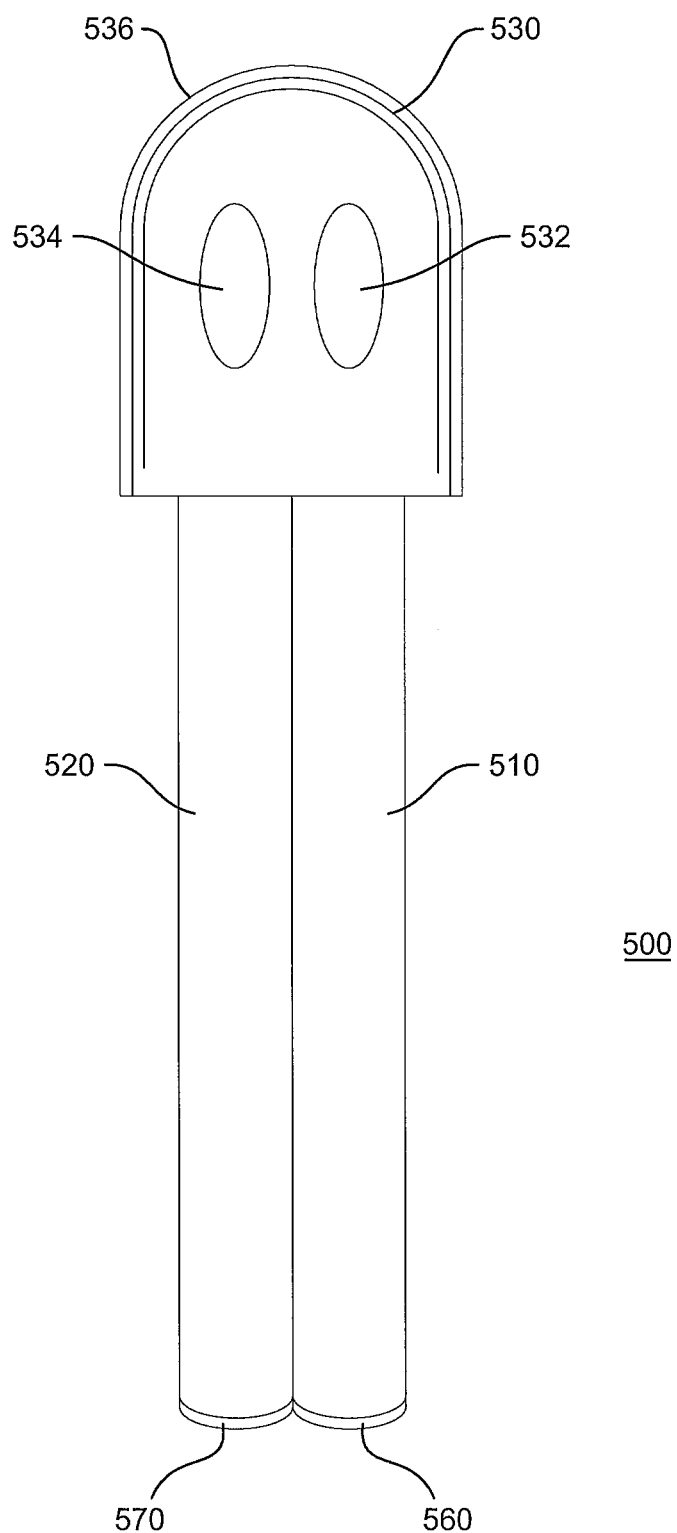
FIG. 6 is a top view of scope holder 500.

FIG. 6 is a top view. From this view, top plug 530 has a first internal channel 532 connected to tube 510 and a second internal channel 534 connected to tube 520. Each internal channel is open to the top and this top plug 530 has an optional rim 536 to help in getting sterile fluid into the internal channels to fill the scope tubes (the rim does not need to extend to the front as fluid that slips over the front edge will go into the basin). Another version of the top plug (not shown) may have a more pronounced and progressive rim so that the top of the top plug becomes a funnel to facilitate pouring sterile fluid into the one or more scope tubes.

The top plug 530 may be made from a material that will not damage the scope as the distal end of the scope makes contact with the top plug 530 when getting aligned for placement into a scope tube. The material choice for the top plug is not based on having high thermal conductivity as thermal conductivity of the top plug is not important. The top plug is intended to guide and protect the scopes being inserted into the assembly. The top plug may be created to be for a single use, may be made for repeated use after sterilization cycles or maybe made as a permanent, integrated component that is connected to the upper portions of the one or more scope tubes and thus goes through sterilizations cycles with the scope tubes if the scope holder is sterilized and reused.

Figure 7:
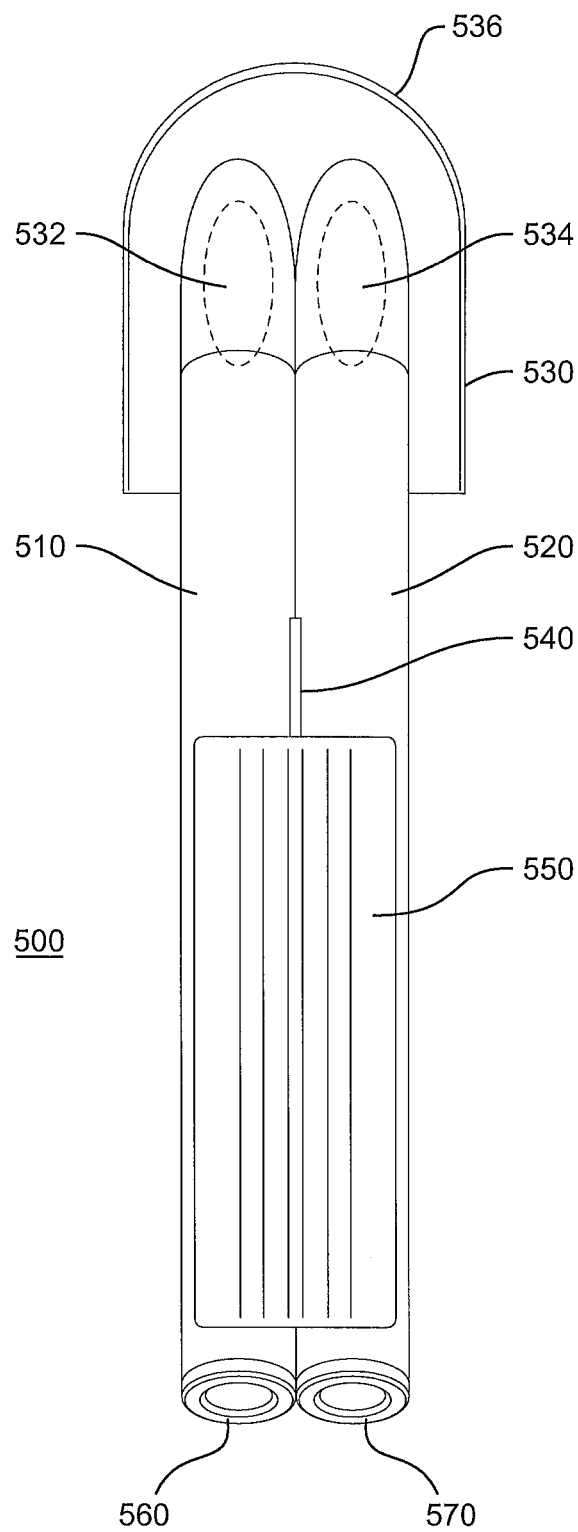
FIG. 7 is a bottom view of scope holder 500 including indications of the hidden lines for the two internal channels (532 and 534).

FIG. 7 is a bottom view including indications of the hidden lines for the two internal channels (532 and 534).

Figure 8:
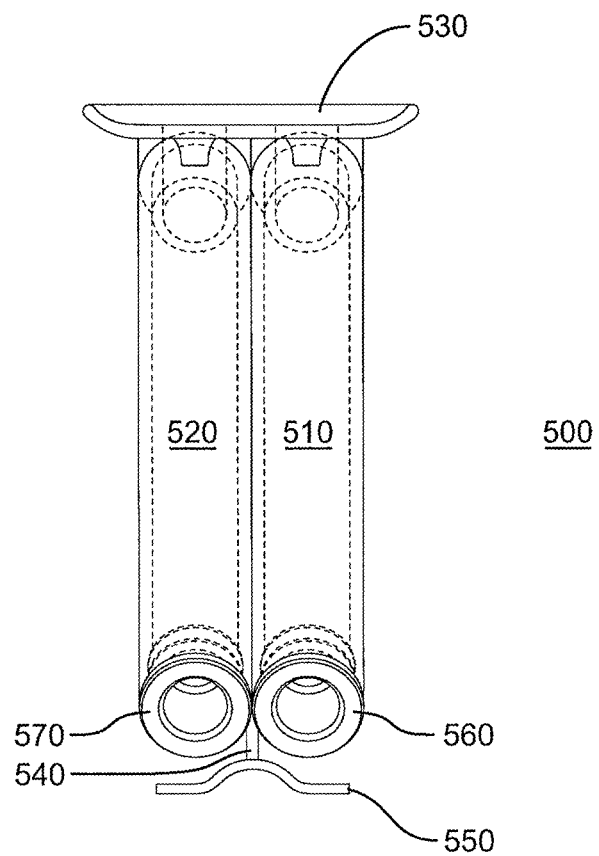
FIG. 8 is a front view of scope holder 500 including internal structures of the tube plugs 560 and 570 and top plug 530.

FIG. 8 is a front view including internal structures of the tube plugs 560 and 570 and top plug 530. Tube plugs may be made from a material that allows the tube plug to be reversibly inserted into the scope tubes to block the bottoms of the scope tubes so that the scope tubes may be filled from the top with sterile fluid to a depth that exceeds the depth of sterile fluid in the basin. The heated sterile fluid in the basin may be used for the traditional range of purposes for use of sterile fluid during and operation and will also serve to help transfer heat to the scope stand 540 and scope tubes 510 and 520. Thus, while the scope stand 540 will obtain some heat through contact with the basin bottom or whatever surface the scope stand rests upon, and this heat will pass to the scope tubes and to the heated fluid in the scope tubes, much of the heat received ultimately by the heated fluid in the scope tubes will pass through the heated liquid.

As a medical scope is inserted into a scope tube, the slope of the scope holder and the presence of sterile fluid will tend to slow the descent of the medical scope. The material and chosen shape of the tube plug may be selected to allow the tube plug to elastically deform when the distal end of a medical scope makes contact with the bottom of the scope tube.

For example the tube plugs may have a frustum shaped projection that is oriented towards the top of the scope tube so that the frustum deforms when the distal end of a medical scope make contact.

While the scope tubes could be made with permanently closed lower ends, it may be advantageous both in reducing the cost of manufacture of the scope holder and in providing access for cleaning to have removable plugs. The heat conductivity of the tube plugs may be much lower than the heat conductivity of the scope tubes as the tube plug may not be needed as a primary path for heat conduction.

Figure 9:
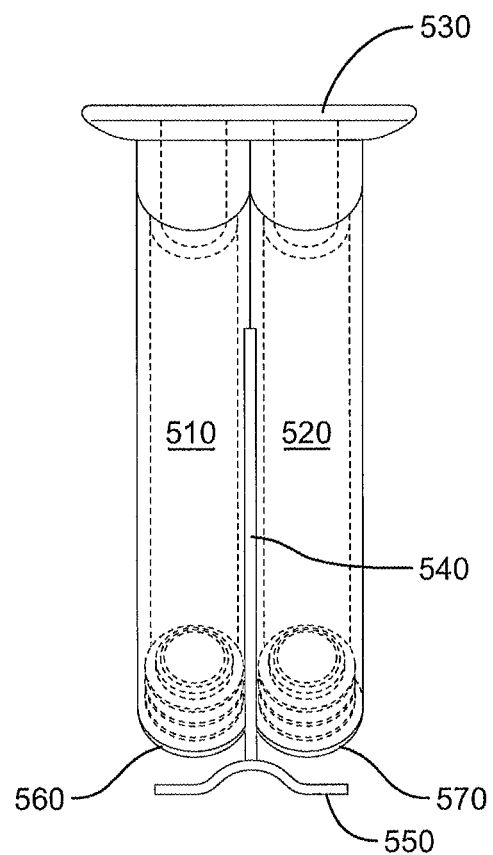
FIG. 9 is a back view of scope holder 500 including internal connections between top plug 530 and scope tubes 510 and 520.

FIG. 9 is a back view including internal connections between top plug 530 and scope tubes 510 and 520.

Figure 10:
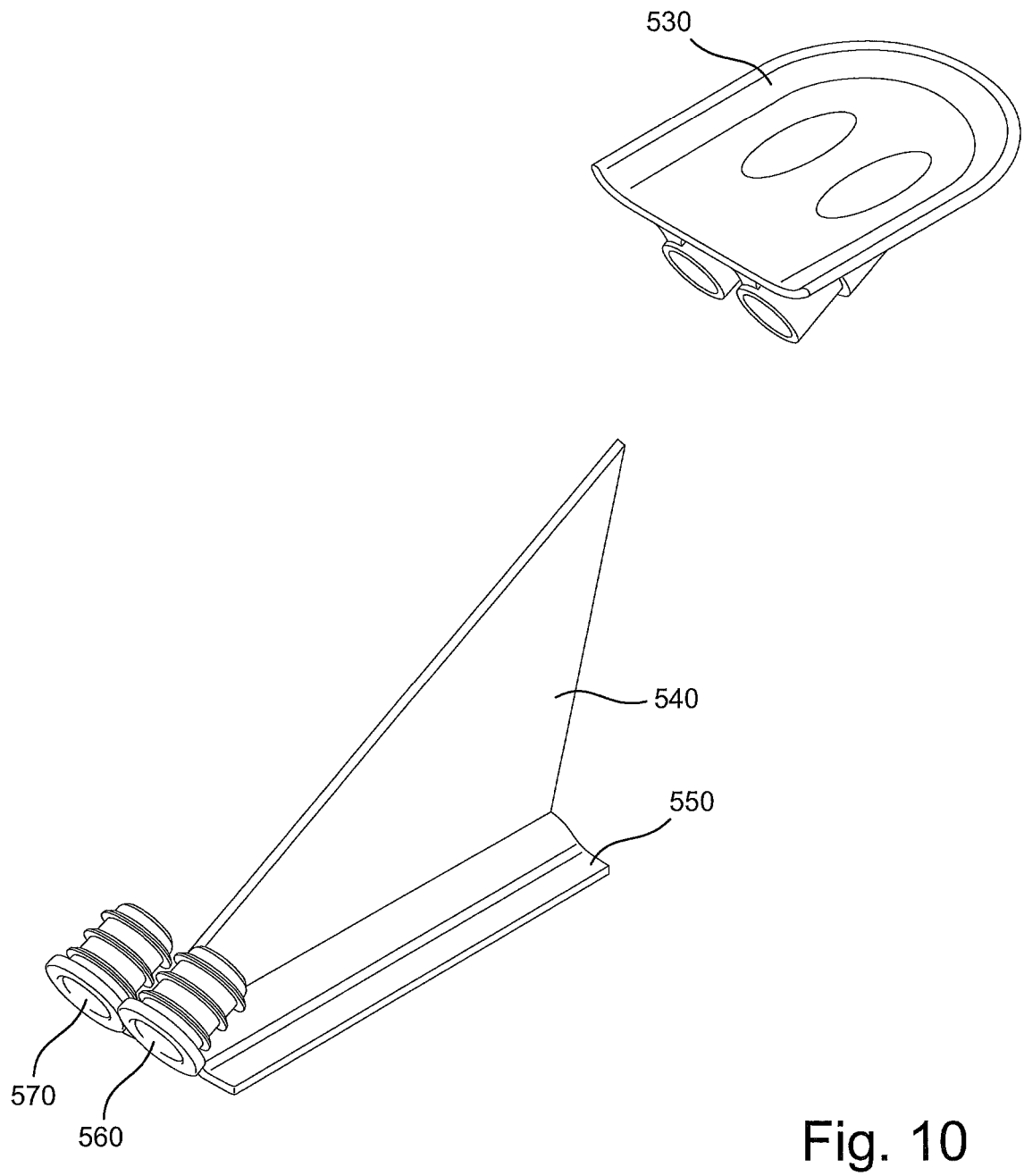
FIG. 10 shows a perspective view of one scope holder 500 with the scope tubes transparent.
Figure 11:
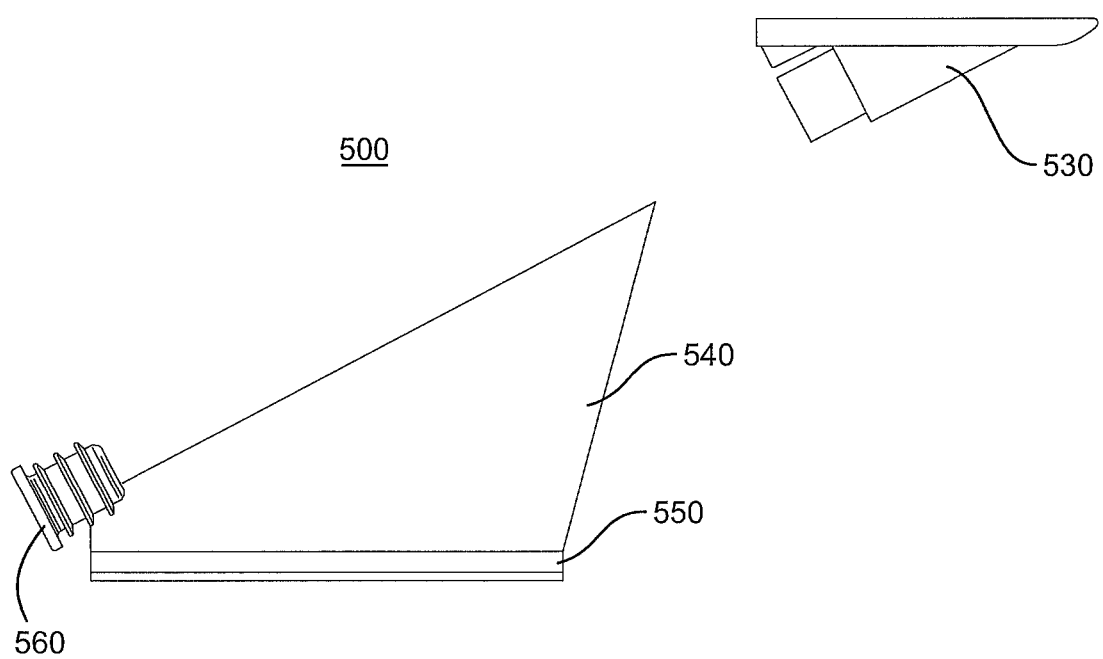
FIGS. 11 and 12 provide side views of scope holder 500 with the scope tubes transparent.
Figure 12:
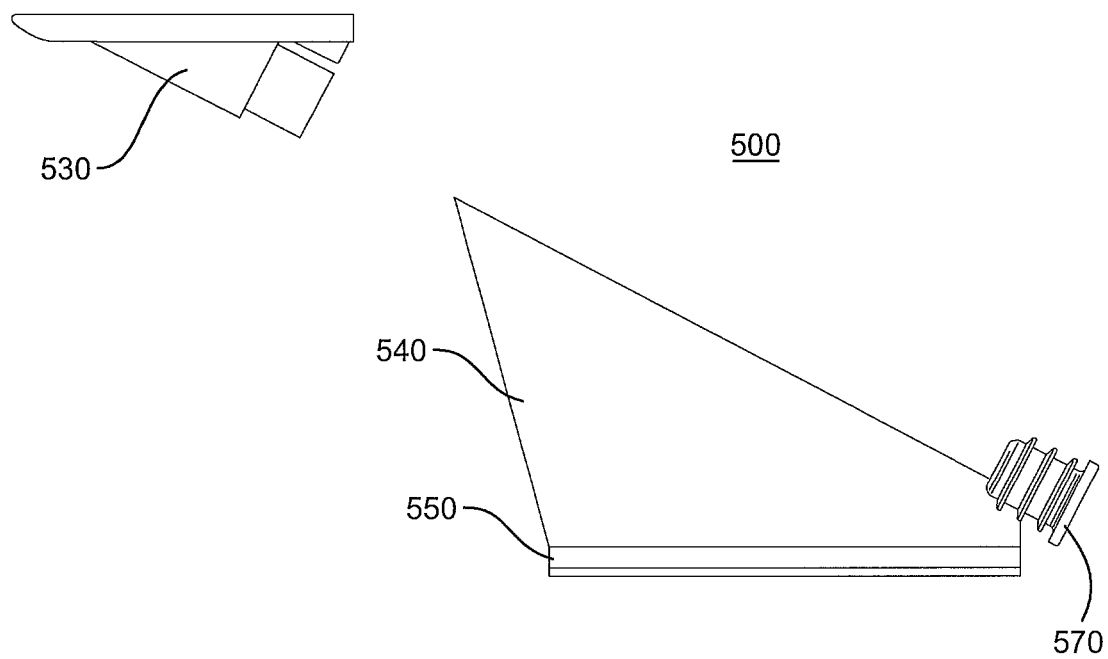
Figure 13:
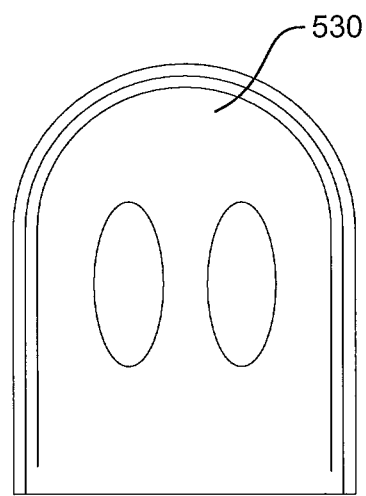
FIG. 13 is a top view of scope holder 500 with the scope tubes transparent.
Figure 13:
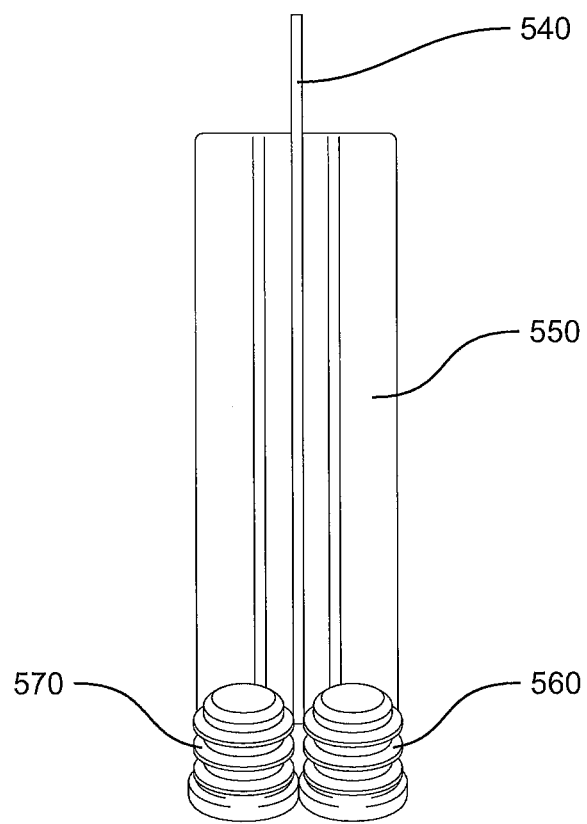
Figure 14:
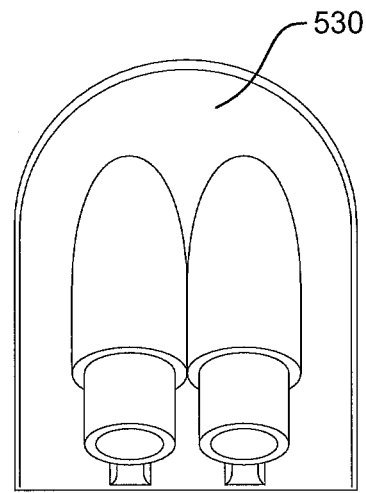
FIG. 14 is a bottom view of scope holder 500 including indications of the hidden lines for the two internal channels (532 and 534) with the scope tubes transparent.
Figure 14:
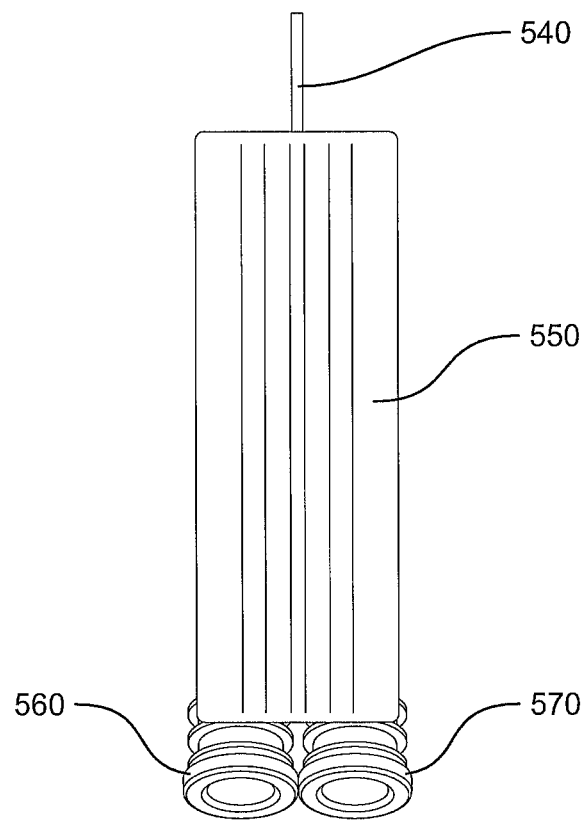
Figure 15:
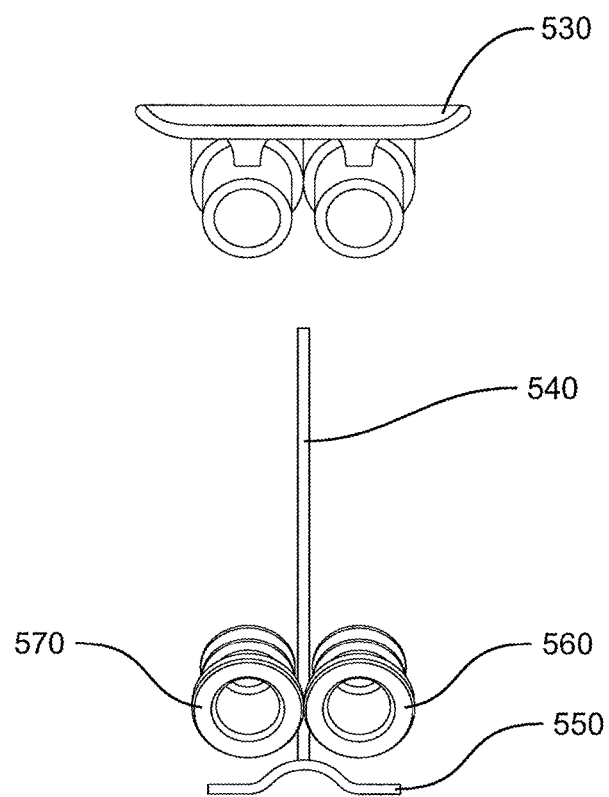
FIG. 15 is a front view of scope holder 500 with the scope tubes transparent including internal structures of the tube plugs 560 and 570 and top plug 530.
Figure 16:
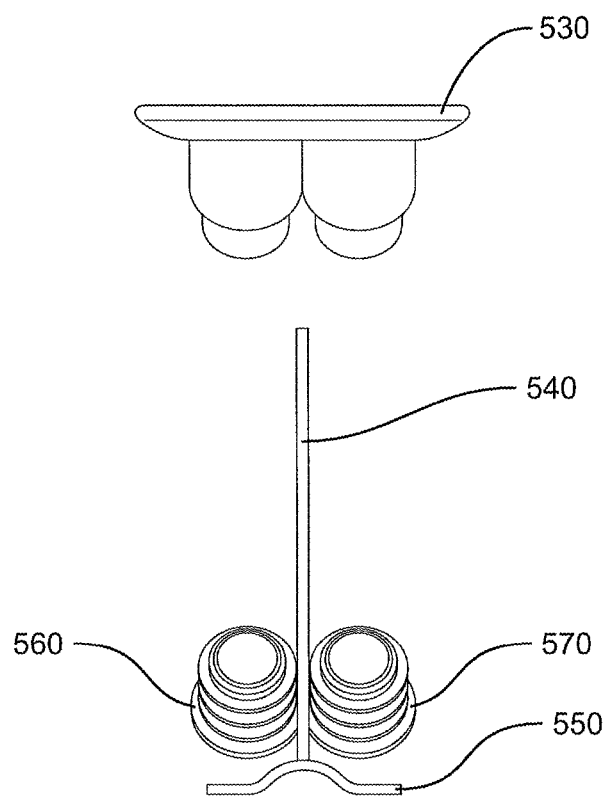
FIG. 16 is a back view of scope holder 500 with the scope tubes transparent.

FIGS. 10-16 repeat the views shown in FIGS. 3-9 but with the scope tubes made transparent so that details of the other components are more apparent. FIG. 10 repeats the view from FIG. 3. FIG. 11 repeats the view from FIG. 4. FIG. 12 repeats the view form FIG. 5. FIG. 13 repeats the view from FIG. 6. FIG. 14 repeats the view from FIG. 7. FIG. 15 repeats the view from FIG. 8. FIG. 16 repeats the view from FIG. 9.

Figure 17:
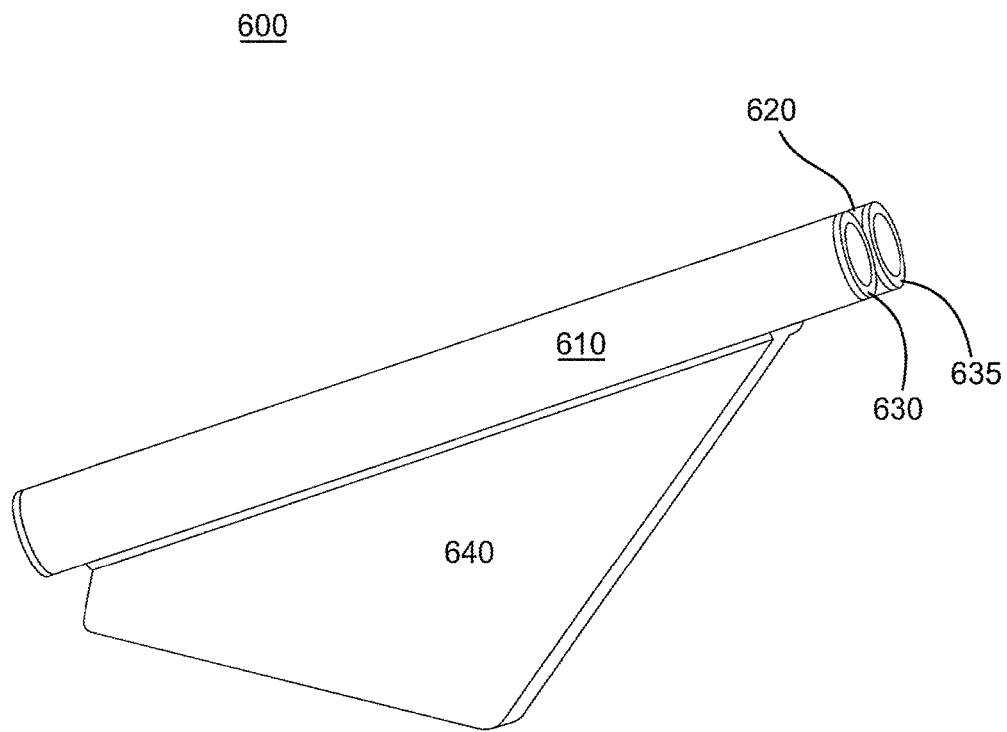
FIG. 17 shows an alternative scope holder 600.

FIG. 17 shows an alternative scope holder 600 with scope tubes 610 and 620, top inserts, 630 and 635, tube plug 660 (tube plug for scope tube 620 is not visible in this view) and base 640. Note that top inserts 630 and 635 serve the function of top plug 530 in guiding and protecting the medical scope as it is introduced into the scope tubes. Thus, the material choices for top plug 530 may apply equally to top inserts 630 and 635. In this instance the top inserts 630 and 635 do not provide assistance in guiding poured sterile fluids into the one or more scope tubes. However, other variations (not shown) may elongate the lower portions of the top inserts 630 and 635 to assist with the fluid guiding function.

Basin Details.

FIGS. 18-24 show a series of views of a basin that may be used in a liquid warming device for basin to interact with certain features of a particular liquid warming device such as described in U.S. Pat. No. 7,128,275 for Liquid Warming Device With Basin.

Figure 18:
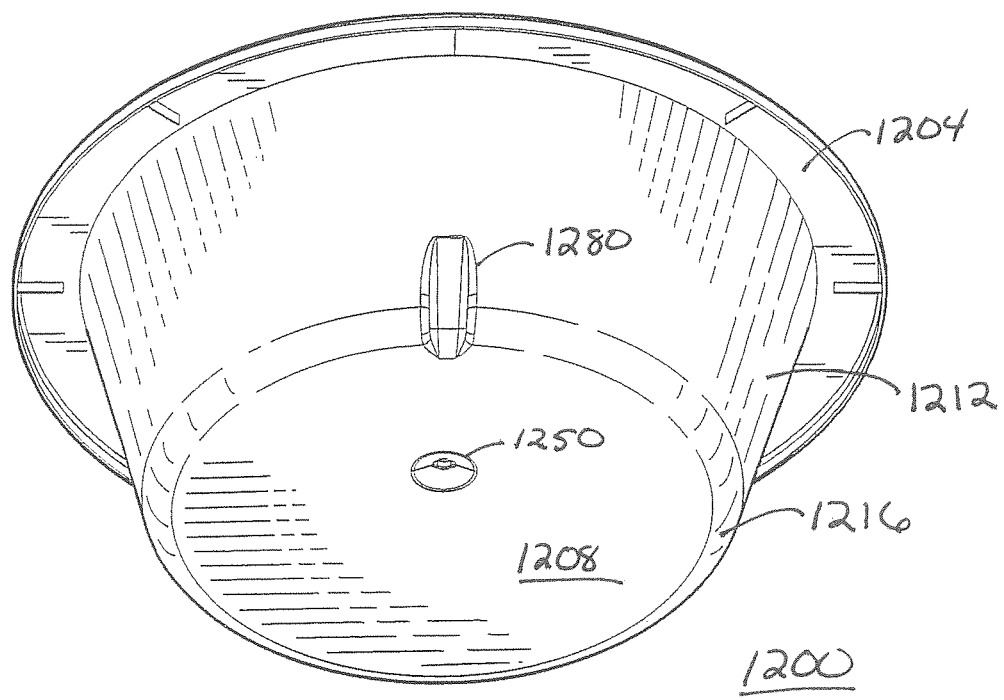
FIG. 18 shows a bottom and side perspective view of basin 1200 with rim 1204, bottom 1208, sidewall 1212, and sloped ring 1216.

FIG. 18 shows a bottom and side perspective view of basin 1200 with rim 1204, bottom 1208, sidewall 1212, and sloped ring 1216. Thermocouple well 1250 is partially visible. An alignment channel 1280 is present at the intersection of the bottom 1208 and a portion of the sidewall 1212. This alignment channel 1280 fits over a corresponding ridge in the fluid warming device (not shown) to provide an aid in aligning the basin 1200 relative to the fluid warming device so that the temperature sensor can be forced into the interference fit in the thermocouple well 1250. (Note that one of skill in the art can appreciate that an alignment channel would be of value even if the thermocouple well does not require the exertion of force for an interference fit.)

Figure 19:
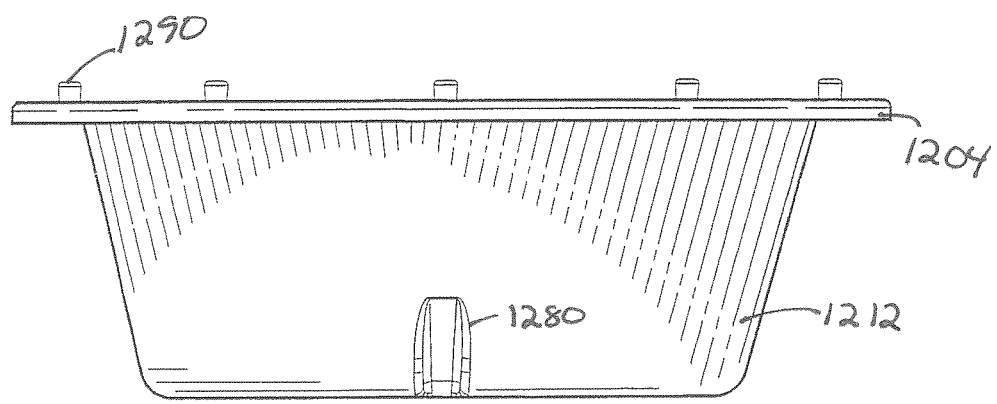
FIG. 19 provides a side plan view of the same basin 1200 with the alignment channel 1280 visible.

FIG. 19 provides a side plan view of the same basin 1200 with the alignment channel 1280 visible. FIG. 19 shows optional rim protrusions 1290 that protrude upward from the top face of the rim 1204. As the rim protrusions may be formed so as to be hollow, the rim protrusions 1290 may be used as an alternative or a compliment to the alignment channel 1280 to position the container in a particular orientation. This would require an interaction with corresponding protrusions from the top surface of the liquid warming device. If the alignment is to be controlled primarily or exclusively by alignment of the rim protrusions 1290 and the corresponding protrusions on the liquid warming device or adapter (discussed below), then it may be advantageous to have an asymmetric pattern of rim protrusions 1290 so that there is only one rotational position that aligns all the rim protrusions 1290 with the corresponding protrusions.

The rim protrusions 1290 may be used to attach accessories to the basin by having one more voids in the accessory that receives one or more of the rim protrusions 1290 to help maintain the position of the accessory relative to the basin 1200.

Figure 20:
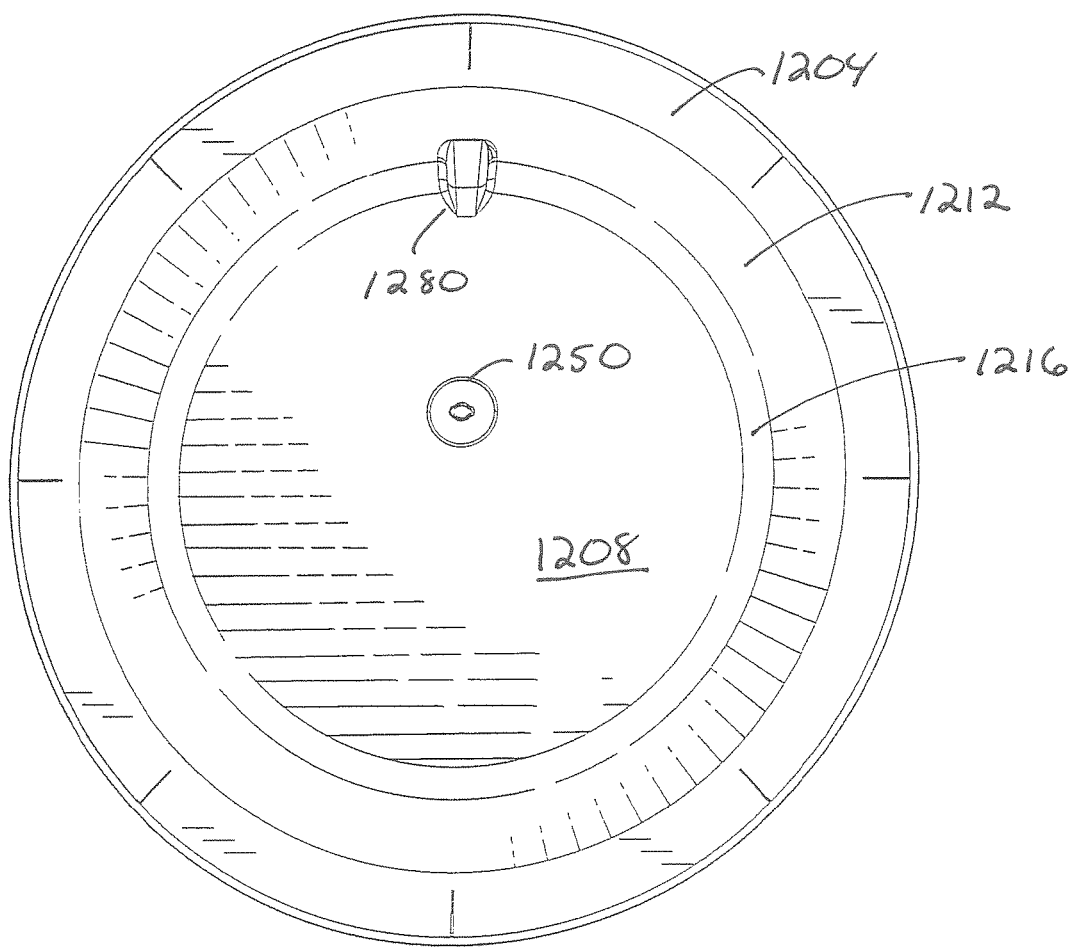
FIG. 20 is a bottom plan view that shows that the center of the thermocouple well 1250 is a winged divot 1254.

FIG. 20 is a bottom plan view that shows that the center of the thermocouple well 1250 is a winged divot 1254. The winged divot 1254 is surrounded by an indentation ring 1258 that interacts with the limit switch actuator. When the basin 1200 is forced down upon temperature sensor 804, the indentation ring 1258 is able to move downward in the fluid warming device to depress the limit switch actuator to cause the limit switch (as described in U.S. Pat. No. 7,128,275) to close and allow for the provision of energy to the heater.

Figure 21:
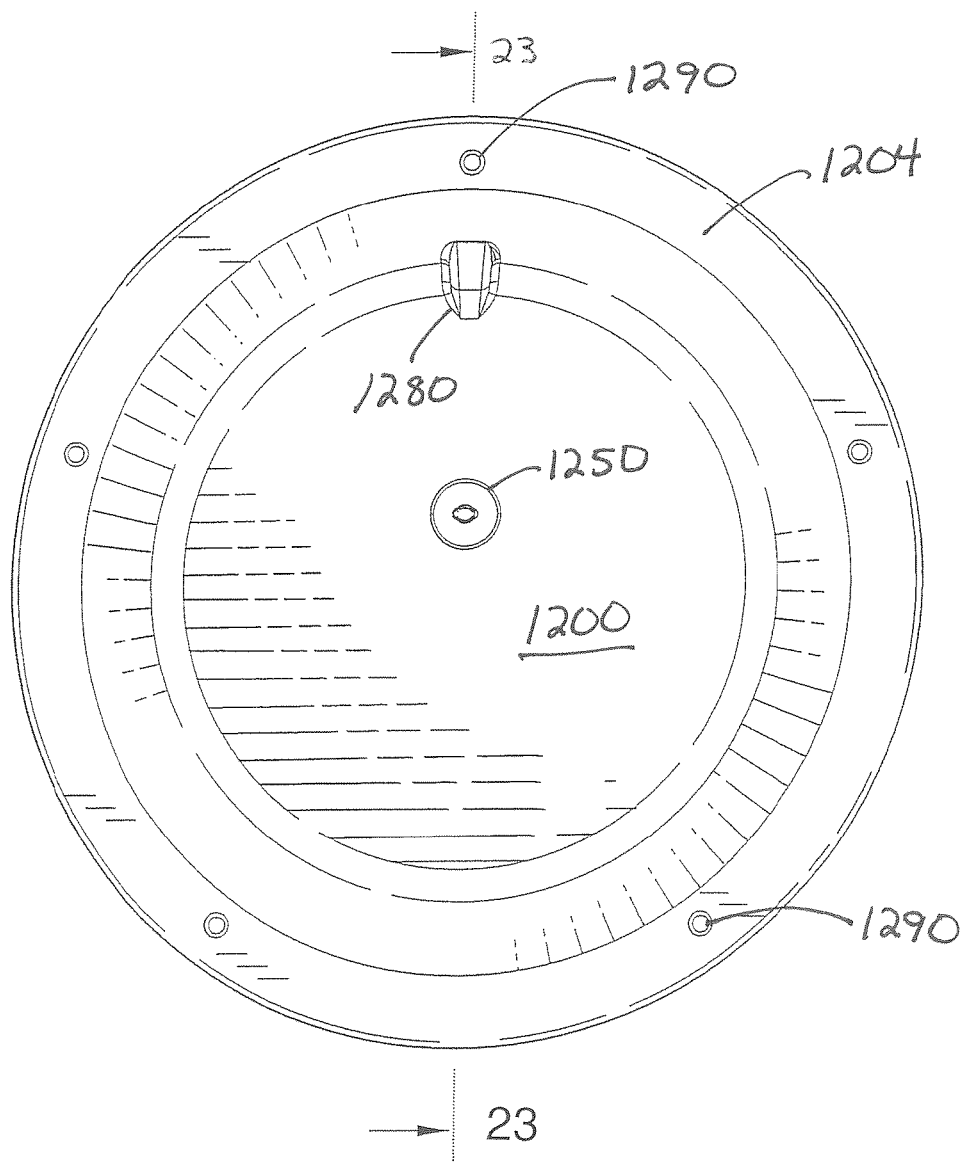
FIG. 21 is a top view of the same basin 1200.

FIG. 21 is a top view of the same basin 1200. Alignment channel 1280 and thermocouple well 1250 extend into the bottom 1208 of the basin 1200 as shown in FIG. 20 but stick out into the fluid holding portion of the basin 1200 as shown in FIG. 21.

Figure 22:
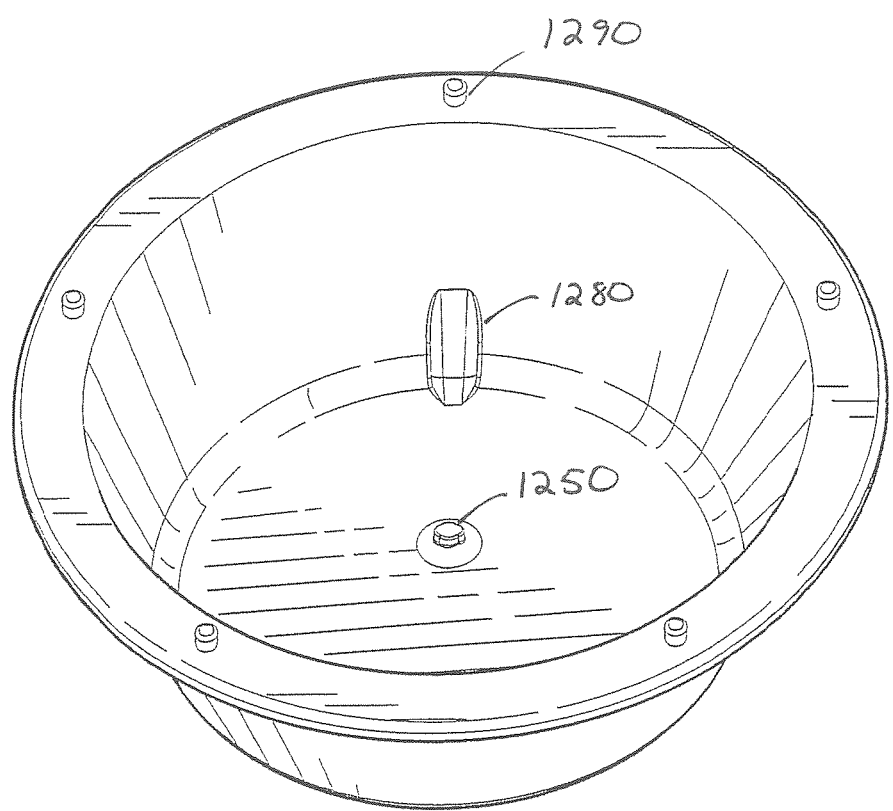
FIG. 22 is a top and side perspective view of the basin 1200.
Figure 23:
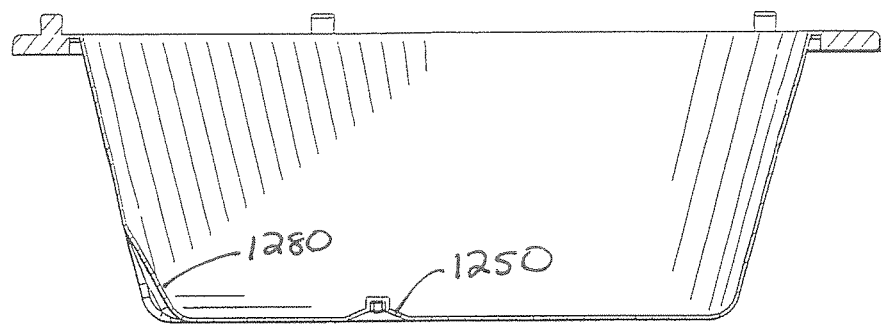
FIG. 23 is a cross section taken through the alignment channel 1280 and the thermocouple well 1250.
Figure 24:
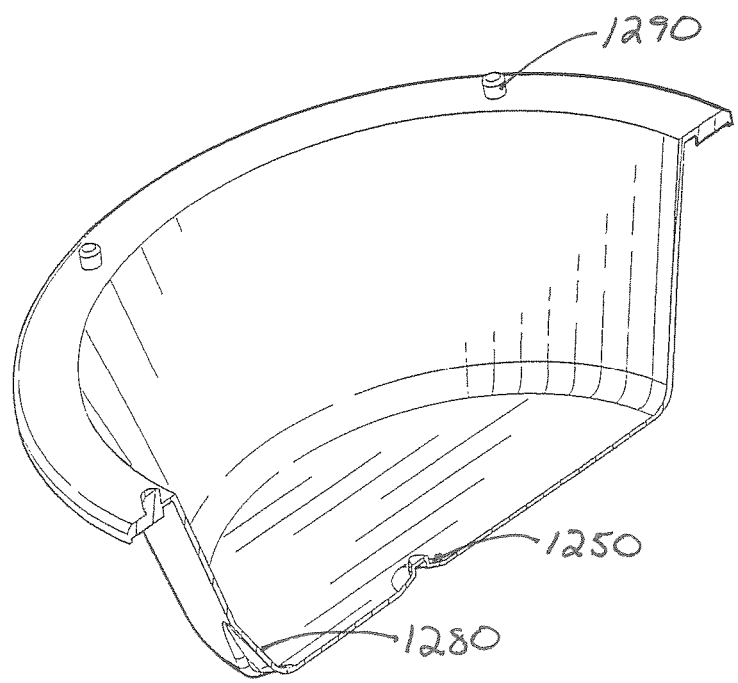
FIG. 24 is a top perspective view of the cross section shown in FIG. 23.

The extension of the thermocouple well 1250 into the basin is easier to see in FIG. 22 which shows a top and side perspective view of the basin 1200. The winged divot 1254 is seen extending above the indention ring 1258. A cross section taken through the alignment channel 1280 and the thermocouple well 1250 is shown in a side view in FIG. 23 and a top perspective view in FIG. 24.

The basin 1200 has the thermocouple well 1250 part way between the sidewall and the center of the basin. One of skill in the art will recognize that placement of the thermocouple well very near the side walls of the basin is less likely to lead to obtaining a representative temperature of the fluid in the container as there is the possibility of edge effects impacting the measurement. However, one can appreciate that the function of the thermocouple well 1250 and the alignment channel 1280 could be combined by placing the temperature sensor and the limit switch actuator in the ridge that interacts with the basin alignment channel 1280 and eliminating the thermocouple well 1250 from the basin. While attractive from the standpoint of simplifying the basin, it is currently thought that a free-standing thermocouple well further towards the center of the basin would provide a better indication of current fluid temperature.

Interactions Between Scope Holder and Basin.

The scope holder base may be adapted to engage with one or more features of the basin 1200. For example, the scope holder base may be adapted to engage with alignment channel 1280 to help stabilize the scope holder. The scope holder base may also be adapted to envelope or rest against the thermocouple well 1250. The scope holder base may be adapted to fit over both the alignment channel 1280 to prohibit lateral movement of the scope holder base and adapted to contact the thermocouple well 1250 so that the scope holder base may not move parallel to the long axis of the alignment channel 1280 so that the scope holder base cannot become disengaged from the alignment channel 1280.

Additionally or alternatively, the scope holder may include a rim piece to engage the rim 1204 of the basin 1200 possibly including one or more rim protrusions 1290.

The stand base 550 may include a ridge of sufficient height and width to allow the scope holder to be placed over known deviations from flat to be found in the basin bottom including potentially the thermocouple well, or the rounded "gate" found in many basins as an artifact of the molding process. This ridge in the stand base 550 is less about affixing the scope holder in a particular place and more about giving options to place the scope holder in a portion of the basin that does not have a flat bottom.

By having the stand base 550 not extend the full length of the scope holder, the scope holder may be placed near the alignment channel 1280 without interacting with the alignment channel 1280. Again this allows freedom of choice in placing the scope holder where it is convenient for the scope users rather than coordinating the placement with the attributes of the liquid warming device.

One of skill in the art will recognize that the concepts of interaction between the scope holder and a basin intended to receive the scope holder may be extended to other basins or features of whatever liquid warming device the scope holder is intended to be used with in order to augment the stability of the scope holder.

Rinsing and Cleaning Scopes.

As a medical scope is used, it may become covered in body fluids and tissue. The medical scope may be cleaned by dunking the distal end of the medical scope into a scope tube. Repeated somewhat rapid motion of the scope within the scope tube will tend to cause the sterile fluid to agitate against anything on the surface of the medical scope. The range of motion of the distal end of the medical scope during dunking does not have to extend down to make contact with a tube plug.

The sterile fluid in the scope tubes may be replaced by dumping out the sterile fluid in the tubes after several uses to clean a medical scope and then pouring in new sterile fluid. The sterile fluid added to the scope tubes partway through a medical procedure may be obtained from containers of sterile fluid that have been heated to the target temperature and maintained at or near the target temperature in an open access sleeve (400 or 410) as shown in FIG. 1 and discussed in co-pending U.S. patent application Ser. No. 11/378,531 for Open Access Sleeve for Heated Fluid Units (incorporated by reference in its entirety herein).

Note that the heated fluid within the scope tubes may or may not be identical to the heated liquid in the basin (outside of the scope tube). For example, a fluid with qualities beneficial to the intended use of cleaning the inserted scope may be used within the scope tubes while a more general purpose sterile liquid may be used in the basin.

Design Choices.

The scope stand base may be made out of a high mass, possibly thick, and highly thermally conductive material. The scope tubes may be made out of a lower mass/thickness and possibly lower thermally conductive material or they may be made out of the same material as the scope stand and stand base. For optimized thermal performance, the lower portion of the scope tubes may be made of a material that has high thermal conductivity to help get heat from the sterile fluid in the basin (outside of the scope tube) to the sterile fluid in the scope tube to expedite heating of an inserted scope. The upper portion of the scope tube may be made of a material with low thermal conductivity to insulate, that is to reduce the heat loss from the upper part of the scope tube to the ambient air (which is likely to be in the range of 68 degrees Fahrenheit).

The stand or base may be shaped with an arch or similar geometry on the bottom to accommodate both the round "gate" resulting from molding the fluid container (basin) and the thermal temperature well. This platform or base shape provides stability while the scope holder sits in the basin.

The base is connected to the scope holder with an angled support member (scope stand 540) that is angled appropriately to allow the more distal aspect of a scope to rest on or near the fluid basin's upper rim. The angled support member is also made of a highly conductive material and/or thickness in order to efficiently transfer heat to the scope holding assembly portion of the device. While a scope holder could be created that aligns the retained scopes essentially vertical, the sloped configuration is currently preferred. One may choose the slope of the scope holder tubes to place the handle of the medical scopes intended for use in this scope holder just beyond the basin rim. Thus, a scope holder for shorter medical scopes may have an angle of 45 degrees with respect to horizontal but a scope holder for much longer medical scopes may have an angle of 70 degrees with respect to horizontal so that the scope handle is not extended too far beyond the outer rim of the basin.

The scope tubes 510 and 520 may be made of one or more hollow tubes or cylinders (or some other suitable shape for the cross section including square, triangular, or other non-round shapes) with openings at one or both ends to allow insertion of scopes and/or fluid and to provide easy access for cleaning. Thus, the word tube as used in this specification and the claims that follow is not limited to round cross sections. The scope tubes are preferably close in cross section to the maximum cross section of the relevant portions of the scopes used clinically so as to require less sterile fluid in the scope tube and to change depth in a more pronounced way as a scope is inserted into the scope tube to heat a larger length of the inserted scope. Thus, selecting a cross section that is larger than but close to the relevant cross section of the scope intended for insertion into the scope holder is desirable from a performance and cost perspective.

While the scope holder used to illustrate the teachings of this disclosure had two scope tubes, the teachings could be applied to having one or more scope tubes. If four scope tubes are required, they could be arranged to be four scope tubes in one layer or in a configuration of two layers of two scope tubes. Likewise, for three scope tubes there could be three scope tubes in one layer or a second layer of just one scope tube. The scope holder may have more than two layers of scope tubes.

While the tube plugs discussed above have been interference fit plugs, they could be attached in other ways such as threaded engagement with the bottom end of the scope tubes. It is desirable that the bottom of the scope tube be reversibly sealed to allow the level of sterile fluid in the scope tube to exceed the level of sterile fluid in the basin. It is desirable to be able to remove the seals from the bottom of the scope tubes to facilitate cleaning the interior of the scope tubes.

What is claimed is:

1. A scope holder for use with a liquid warming device, the scope holder for receiving a distal end of at least one medical scope to immerse at least a portion of the medical scope in a heated fluid, the scope holder comprising:
   at least one scope tube having:
      an open proximal end; and
      a closed distal end;
   a scope holder frame including a scope holder base to support the at least one scope tube so as to position the open proximal end of at least one scope tube above the closed distal end of the at least one scope tube so that a heated fluid within the scope tube may be maintained at a fluid level above a liquid level of a heated liquid outside of the scope tube; and
   the scope holder adapted to allow an average temperature of the heated fluid within the scope tube to respond to heat input from the liquid warming device maintaining the heated liquid outside the scope tube near a target temperature through operation of a control system.

2. The scope holder of claim 1 wherein the heated fluid and the heated liquid are the same material although separated by the walls of the at least one scope tube.

3. The scope holder of claim 1 wherein the scope holder frame maintains a long axis of the at least one scope tube at an oblique angle with respect to the scope holder base.

4. The scope holder of claim 3 wherein the scope holder frame maintains the long axis of the at least one scope tube at an oblique angle with respect to the scope holder base in a range of angles from about 45 degrees to about 70 degrees where 70 degrees is closer to vertical than 45 degrees.

5. The scope holder of claim 1 wherein the distal end of at least one scope tube as a removable seal.

6. The scope holder of claim 5 wherein the removable seal is a tube plug.

7. The scope holder of claim 6 wherein the tube plug is adapted to elastically deform when a distal end of a medical tube is dropped into a scope tube and contacts that tube plug.

8. The scope holder of claim 1 further including a top plug with a channel to allow a distal end of a medical scope tube to enter a scope tube and a rim around at least a portion of the top plug to facilitate pouring of fluid into the scope tube.

9. The scope holder of claim 1 wherein the scope holder is adapted to engage with an alignment channel of a removable basin to limit lateral movement of the scope holder.

10. The scope holder of claim 1 wherein the scope holder is adapted to engage with a thermocouple well of a removable basin to limit lateral movement of the scope holder.

11. The scope holder of claim 1 wherein the scope holder is adapted to engage with a rim of a removable basin to limit lateral movement of the scope holder.

12. The scope holder of claim 11 wherein the scope holder is adapted to engage with at least one rim protrusion on the rim of the removable basin to limit lateral movement of the scope holder.

13. The scope holder of claim 1 wherein the scope holder base has an indentation so that the scope holder may be placed over a raised feature on an interior of a basin.

14. The scope holder of claim 1 wherein at least one scope tube has a cross section taken perpendicular to a long axis of the scope tube and the cross section is not a circle.

15. The scope holder of claim 1 wherein at least part of the at least one scope holder tube is made of a material with high thermal conductivity to promote movement of heat from the heated liquid to the heated fluid.

16. The scope holder of claim 1 wherein a first part of the at least one scope tube is made of a first material of a first thermal conductivity and a second part of the same scope tube is made of a second material of a second thermal conductivity lower than the first thermal conductivity so that the first part promotes heat ingress into the heated fluid from the heated liquid and the second part with lower thermal conductivity partially insulates a portion of the heated fluid from ambient air.

* * * * *